United States Patent [19]
Hildebrand et al.

[11] Patent Number: 5,866,789
[45] Date of Patent: Feb. 2, 1999

[54] FATTY ACID ALTERATION BY A 9 DESATURASE IN TRANSGENIC PLANT TISSUE

[75] Inventors: David F. Hildebrand; W. Scott Grayburn, both of Fayette County, Ky.

[73] Assignee: Pioneer Hi-Bred International, Inc., Des Moines, Iowa

[21] Appl. No.: 588,540

[22] Filed: Jan. 18, 1996

Related U.S. Application Data

[63] Continuation of Ser. No. 376,534, Jan. 20, 1995, abandoned, which is a continuation of Ser. No. 247,622, May 23, 1994, abandoned, which is a continuation of Ser. No. 816,288, Dec. 31, 1991, abandoned.

[51] Int. Cl.$^6$ ............... A01H 5/00; C12N 5/04; C12N 15/82
[52] U.S. Cl. ........... 800/205; 435/172.3; 435/320.1; 435/419; 800/DIG. 40; 800/DIG. 17; 800/DIG. 26; 800/DIG. 69
[58] Field of Search .............. 435/320.1, 172.3, 435/240.4, 419; 800/205, DIG. 17, DIG. 26, DIG. 40, DIG. 69

[56] References Cited

U.S. PATENT DOCUMENTS 5,057,419  10/1991  Martin et al. .

OTHER PUBLICATIONS

The American Heritage Dictionary, Second College Edition, Houghton Miflin, Boston, 1982, p. 1273.

Morphology of Plants, 3rd Edition, Bold, Harper & Row, NY, 1973, p. 7.

Wada, et al (Sep. 1990) Nature *347*:200–203.

Knauf (Feb. 1987) Tibtech *5*:40–46.

Weising, et al (1988) Ann. Rev. Genet *22*:442–443.

Strittmatter, et al (Feb. 1988) Journal of Biological Chemistry 263(5):2532–2536.

Somerville, et al (Apr. 5, 1991) Science 252 (5002):80–87.

*Primary Examiner*—Elizabeth F. McElwain
*Attorney, Agent, or Firm*—Foley & Lardner

[57] ABSTRACT

A method for the alteration of synthesis of fatty acids and the corresponding compositions of triacylglycerols in plants is provided. Plant tissue transformed with a fatty acid CoA desaturase gene obtained from an animal or yeast source shows a decrease in saturated 16 and 18 carbon fatty acids with a corresponding increase in monounsaturated 16 and 18 carbon fatty acids in transformed calli, leaves and seeds.

20 Claims, 8 Drawing Sheets

FATTY ACID ALTERATION BY A 9 DESATURASE IN TRANSGENIC PLANT TISSUE

This application is a continuation application of U.S. Ser. No. 08/376,534, filed Jan. 20, 1995, now abandoned, which was a continuation application of U.S. Ser. No. 08/247,622, filed May 23, 1994, now abandoned, which was a continuation application of U.S. Ser. No. 07/816,288, filed Dec. 31, 1991, now abandoned.

TECHNICAL FIELD

The present invention relates to the alteration of synthesis of fatty acids and the corresponding compositions of triacylglycerols in plants via use of a fatty acid-Coenzyme A or Δ9 desaturase gene.

BACKGROUND OF THE INVENTION

Plants naturally produce an assortment of fatty acids and synthesize an even wider assortment of lipids, including mono-, di- and triacylglycerols, phospholipids, glycolipids, and others, from the fatty acids they produce. The specific assortment of lipids made by any particular plant is determined by both the genotype of the plant and the plant's response to environmental factors such as heat, cold, drought, etc. However, regardless of the environmental conditions, a plant can never produce a fatty acid or lipid composition for which it does not have the necessary biochemical machinery, and such biochemical pathways are ultimately determined by genotype. Traditional methods of genetic modification involve genetic recombination processes which are directed by the plant breeder at the whole plant level. These methods, while well characterized and straightforward to conduct, typically produce incremental improvements in oil content and composition by optimizing the native biochemistry, rather than by creating new biochemical pathways.

At the same time, because of their influence on food quality and significance in biological processes, there is continuing interest in the alteration of fatty acid desaturation mechanisms in plants. The properties of fats and oils are determined by their fatty acid composition, which in turn affects nutritional quality and oxidative stability. Likewise, the specific structures and compositions of other plant lipids which the plant synthesizes from fatty acids are dependent upon the makeup of the fatty acid pool which is available as precursors to the biosynthesis of those lipids.

Recently there has been interest in reducing the content of saturated fatty acids in foods. Medical and nutritional research have led many food and food component producers to want certain compositions in their fat and oil based foods and food components. Those desired compositions are frequently high in mono- and polyunsaturated fatty acids and corresponding triacylglycerol stores, or are low in saturated fatty acids and saturated fatty acid-based triacylglycerols. Industrial users of plant-derived fats and oils also have preferences for the specifications of feedstocks used in their industrial processes, and such specifications often call for large percentages of a single fatty acid moiety. Often the preferred fatty acid moiety is an unsaturated fatty acid moiety such as palmitoleate, oleate, linoleate, or linolenate. Unfortunately, nature does not cooperate by providing oilseed plants which produce the preferred compositions. Efforts have therefore been initiated to develop oilseed varieties and hybrids which yield vegetable oils with higher monounsaturated fatty acid contents. However, in view of the incremental nature of whole-plant genetic methods, the need and desire continue to exist for compositions and methods which can affect and create biochemical pathways at the single-gene level through genetic engineering.

Even when traditional plant breeding methods are successful in altering fatty acid composition in the lipids of a plant variety, the native biochemical pathways of the plant still exhibit all of their art-recognized characteristics and limitations. Thus, for example, oilseed crops which have been improved by plant breeding exhibit the usual responses to environmental variations. These responses include a tendency to produce higher percentages of saturated fats under warmer growing conditions and higher percentages of unsaturated fats under cooler growing conditions, making the reliable production of oilseeds having a particular fatty acid composition as difficult as predicting the weather. Thus, it would also be highly desirable to have means for compensating for these environmental influences. Little effort has been invested to date toward that objective.

Finally, there is a continuing desire to improve and extend the environmental range of crop plants. Some oilseed species originated in temperate, subtropical and tropical regions and are poorly adapted to cooler production areas. Even oilseeds which are suitable for cooler climates can benefit from further adaptation, since moving up the planting time in the spring and extending the growing season in the summer and fall can sometimes be exploited for higher crop yields. Plant breeders have focused a great deal of attention on one aspect of the necessary climatic adaptation, maturation rate, but another important aspect of climatic adaptation is chilling tolerance (as distinguished from freezing tolerance.)

DISCLOSURE OF THE INVENTION

Figure 1:
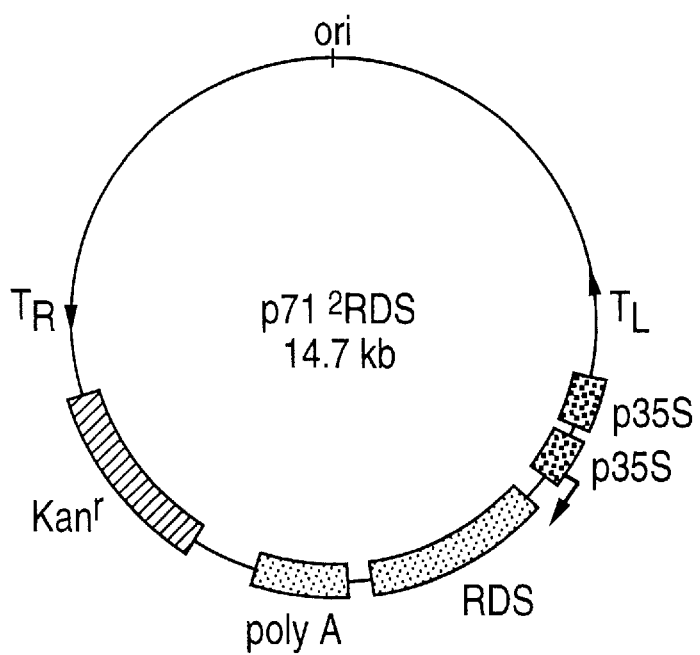
FIG. 1 is a plasmid map of the plasmid used in the transformation work described in Examples 1–5.

The present invention provides a chimeric gene construct for genetic modification of plants to increase their production and content of unsaturated fatty acids and the corresponding lipids produced from those fatty acids. The chimeric gene construct comprises a sequence which codes substantially solely for a fatty acid-Coenzyme A or Δ9 desaturase enzyme. The coding sequence is operatively linked to upstream and downstream regulatory components which act to cause expression of the gene (production of the enzyme) in plant cells. Unsaturated fatty acids are produced by different enzymes in plant and animal cells, and there is little structural or sequence homology between the desaturases found in animal and yeast cells and the corresponding enzymes in plants. However, it has now been found that when a construct according to this invention, containing a gene for a Coenzyme A-dependent desaturase, is introduced into plant cells by a conventional transformation method, such as microparticle bombardment, Agrobacterium infection, or microinjection, the gene is expressed in the cells under control of the juxtaposed plant regulatory sequences and successfully interacts with the biosynthetic machinery which is naturally present in the plant cells to catalyze desaturation of the naturally produced palmitate and stearate moieties, yielding palmitoleate and oleate. By causing formation of greater amounts of these monounsaturated compounds, this invention also favors the production of other fatty acid moieties of higher degrees of desaturation for which the monounsaturates serve as precursors. These unsaturated moieties are identical to naturally occurring unsaturated fatty acid moieties and can then be incorporated into triacylglycerol storage lipids in the plant tissues via existing biochemical pathways. In this way the percentage composition of the unsaturated fatty acid moieties and the corresponding triacylglycerols (as well as mono- and diacylglycerols, phospholipids, and other fatty acid-derived lipids) is increased. Thus, this invention also provides plant cells and whole plants having increased percentage compositions of unsaturated fatty acid moieties and corresponding fatty acid-derived lipids, in which the plant cells contain a chimeric gene construct according to this invention. Also provided are methods for increasing the percentage compositions of unsaturated fatty acid moieties and corresponding fatty acid-derived lipids in plant cells and whole plants, comprising the step of inserting into such plant cells or the cells of such whole plants a chimeric gene construct according to this invention.

Considering the tobacco plant as a model system, there are two major saturated fatty acids found in tobacco leaves, palmitic (16:0) and stearic (18:0) acids. Using these molecules as substrates, double bonds are formed one at a time by consecutive desaturation reactions. These reactions involve desaturases, which catalyze hydrogen removal, and electron transport components. In plants, the first desaturation step is catalyzed by a soluble enzyme localized in chloroplasts. In higher plants, 16:1 and 18:1 are formed from palmitic and stearic acids esterified to acyl carrier protein (ACP) or certain glycerol lipids. Subsequent desaturation reactions can occur in both plastids and the endoplasmic reticulum, with different genes apparently encoding the enzymes found in the different subcellular locations. It has been estimated that there are at least eight genes controlling the activity of specific desaturases in the plant system.

In vitro studies of safflower desaturase show a requirement for ferridoxin added to *E. coli* extracts. Similar results were found for avocado desaturase.

In a preferred embodiment of this invention, the stearyl coenzyme A desaturase from rat is used. This is a Δ9 desaturase that in the normal rat requires electrons from reduced cytochrome $b_5$ in the cytoplasm. However, in the normal plant these reactions normally occur via a Δ9 desaturase in the chloroplast. Intermembrane forms of fatty acids in the cytoplasm can exist as CoA derivatives. It has now been discovered that a desaturase from an organism in another kingdom can function effectively with essential biopathway components supplied by a plant despite the wide divergence between the gene and protein sequences and structures in the two kingdoms. Thus, this invention involves creation of a biochemical pathway in the plant that normally uses the CoA forms of fatty acids and functions in the cytoplasm rather than the chloroplast. The results obtained with this invention indicate that cytochrome $b_5$ and cytochrome $b_5$ reductase present in plants can substitute for these corresponding components normally found in the functional rat desaturase complex.

It has also been observed that the synthesis of unsaturated fatty acids and the lipids derived therefrom is a common plant response to cold environmental conditions. Bacteria with altered membrane fatty acid compositions have been shown to survive at lower temperatures than wild-type strains. While not intending to be limited by theory, it is believed that synthesis of these fatty acids and lipids, which remain liquid at lower temperatures than their saturated counterparts and therefore help to maintain membrane fluidity at low temperatures, helps the plant to tolerate those lower temperatures. Thus, the present invention also offers the opportunity to enhance the cold tolerance of plants by augmenting their natural ability to synthesize unsaturated fatty acids and lipids derived therefrom.

Conversely, it will be understood that plants also tend to synthesize fully saturated fatty acids and lipids derived therefrom under warmer environmental conditions. On the other hand, the desaturase genes used in this invention are typically derived from animals or yeasts, and therefore function quite effectively at the warmer temperatures normally provided by those natural host organisms. Thus, the present invention also provides the ability to offset or compensate for the effects of warmer growing temperatures on lipid composition in oilseed plants by providing a desaturase gene which is more active at higher temperatures and thus produces greater quantities of fatty acid desaturation products with increasing temperature.

INDUSTRIAL APPLICABILITY

While any plant species can be modified using the expression cassette and methods of this invention, including without limitation species from the genera Fragaria, Lotus, medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Triticum, and Datura, Triticum the fatty acid modifications provided by this invention are expected to be used to best advantage in oil-bearing crops such as soybean, sunflower, rapeseed, safflower, peanut, corn, flax, Chinese tallow tree, jojoba, and palm.

The fatty acid-Coenzyme A desaturase gene can be cloned from any suitable animal or yeast host, since it has been determined that the sequence of this gene is highly conserved across mammalian species and there are even regions of homology between mammalian and yeast genes. Genes encoding the desaturase catalyzing the 18:0 to 18:1 step have been cloned from rat, mouse, and yeast. The Human Genome Project will ultimately produce the coding sequence for the human fatty acid-CoA desaturase, which can be used if desired. On the other hand, no detectable identity has been found between the amino acid sequence of the rat stearyl CoA desaturase (used in the transformation work described herein) and castor (*Ricinus communis*) stearyl-ACP desaturase, so the needed Coenzyme A-dependent gene cannot be obtained from plants.

By "fatty acid-derived lipids" herein is meant any naturally occurring plant lipid which has as a precursor a saturated or unsaturated C12 or higher fatty acid synthesized in the plant. These include, without limitation, mono-, di- and triacylglycerols, phospholipids such as phosphatidylcholine and phosphatidylethanolamine, glycolipids and other lipids of leafy tissues, and others. By converting the naturally occurring fatty acid "feedstocks" for the synthesis of these compounds from saturated to unsaturated, this invention causes the natural biochemical pathways present in the plant to favor the production of the corresponding unsaturated fatty acid-derived lipids.

The following examples illustrate the practice of the present invention without intending to be limitative thereof.

EXAMPLE 1

Construction of the plant expression plasmid.

The cDNA for stearyl CoA desaturase from rat consists of a 1.1 kb coding sequence followed by a 3.5 kb untranslated sequence. The gene used in the examples herein codes for amino acids 3 to 356. The plasmid pDs3–358, constructed as described in *J. Biol. Chem.*, 263:2532–2536, was provided by P. Strittmatter. This was digested with BamHI and SstI to release a 1.2 kb fragment that contained the rat desaturase gene. This was ligated to Bluescript SK+ (Stratagene) digested with BamHI and SstI. This plasmid was then digested with HindIII and SstI to release a 1.2 kb fragment. The plant expression vector pKYLX71:35S is a derivative of pKYLX71 in which the CaMV 35S promoter was replaced with a 35S promoter containing a duplication of bases −416 to −90 relative to the transcription initiation site. This plasmid was digested with HindIII and SstI, treated with calf intestinal alkaline phosphatase, and ligated to the 1.2 kb fragment described above to create p71$^2$RDS. In addition to the structural gene for rat desaturase, this plasmid contains the neomycin phophotransferase gene (conferring kanamycin resistance), a broad host range RK2 replication origin, T-DNA borders, and a polyadenylation signal. A map of this plasmid is shown in FIG. 1. The control plasmid lacked the rat desaturase structural gene but was otherwise identical. Competent *E. coli* TB1 were transformed with the plasmids. Single colonies were recovered from LB plates supplemented with 50 mg/L kanamycin and 12.5 mg/L tetracycline. Colonies were transferred to liquid cultures and DNA was prepared by alkali lysis. Plasmids with the expected size were used for further experiments.

EXAMPLE 2

Plant Transformation.

Plants of *Nicotiana tabacum* cv. 'Xanthi' were transformed using cocultivation with *Agrobacterium tumefaciens* as generally practiced (see, e.g. the 1985 article by Horsch et al., *Science* 227:1229–12231) except leaf strips were used instead of disks. Selection for resistance to kanamycin was at done at a concentration of 100 mg/L. Callus induction, shooting, and rooting all occurred in the presence of kanamycin. Mefoxin was included in media at 300 mg/L to inhibit *Agrobacterium tumefaciens* division.

The plasmids pKYLX71:35S and p71$^2$RDS were mobilized from *E. coli* to *A. tumefaciens* strain LBA4404 using triparental crosses using pRK2013 as the helper plasmid.

EXAMPLE 3

Plant DNA Isolation and Sequence Amplification.

Total plant DNA was isolated from green leaves using acidified guanidinium thiocyanate extraction. After total plant nucleic acids were mixed in 4 M LiCl and centrifuged, the supernatant (that contained the DNA) was removed to a new tube and precipitated with two volumes of ethanol. DNA was then centrifuged, washed with 70% ethanol, dried under vacuum, and resuspended in 1 mM Tris, 0.1 mM EDTA pH 7.5.

PCRs were performed in a total volume of 20 $\mu$L and contained 200 ng total leaf DNA, 11 ng primers (5'ACGTGGATCCACCATGCCGGCCCACATGCTC 3') and (5'GCTACTCTTGTGGCTCCC 3'), 1 mM dATP, dCTP, dGTP, and dTTP, 50 mM KCl, 10 mM Tris pH 8.3, 1.5 mM MgCl$_2$, 0.01% gelatin, and 1 unit of Taq DNA polymerase (AmpliTaqTM DNA polymerase, Perkin-Elmer Cetus). A negative control consisted of all the same components with the exception of the plant DNA. Another negative control included DNA from kanamycin resistant plants transformed with the vector used for plant transformation (pKYLX71:35S) but without the desaturase sequence. Reaction mixtures were covered with mineral oil and placed in a thermal cycler (Lab-Line). The temperature was cycled to 95° C. for 2 sec (denaturation), then to 64° C. and 59° C. each for 2 sec (annealing), and then to 72o for 180 sec (extension) for a total of 30 cycles. PCR products were fractionated on a 0.8% agarose gel in TAE running buffer. Size markers were 1 kb DNA ladders (BRL).

EXAMPLE 4

Lipid Fractionation and Fatty Acid Analysis.

Leaf tissue (approximately 0.5 g) was placed in 3 mL chloroform:methanol (2:1) and ground in a Tissumizer (Tekmar). Solvents were then concentrated in a Speedvac and fractionated on a silica gel 60 plate for PC isolation. Spots were scraped and methyl esters were prepared in sulfuric acid/methanol as described below. Leaf samples used for dry weight calculations were lyophilized.

Methyl esters of total fatty acids were prepared in glass tubes from 100–200 mg of callus tissue that was ground in 2 mL 1% sulfuric acid in methanol with a tissumizer as described above or with glass rods. Leaves prepared for total fatty acid analysis were not ground. Transesterification proceeded at 80° C. until approximately 0.2 mL of the methanol remained. Heptadecanoic acid (17:0; 1 mg/mL in hexane) was added as an internal standard directly to plant tissue at 0.1 mg per gram tissue fresh weight. Hexane was allowed to evaporate for about 10 min. prior to tissue extraction. Quantitation of total plant fatty acids was determined by a comparison of peak areas on chromatograms with heptadecanoic acid areas. For quantitation of fatty acids from lipids fractionated on TLC plates, 25 mg nonadecanoic acid (19:0) was added to each spot prior to scraping. Fatty acid methyl esters were analyzed by gas chromatography as described by Dahmer et al., *J. Amer. Oil Chem. Soc.* 66:543–548 (1989) except that a Hewlett Packard FFAP column was used.

Standards for PC, FFA, TG, 16:0, etc. were from Sigma. Leaves from the FadC mutant of *Arabidopsis thaliana* can accumulate 16:1 [*Science* 252:80–87 (1991)]. FadD mutant leaves can accumulate 16:2 with a corresponding reduction in 16:3. Extracts from these and wild type leaves were used to determine the retention times for 16:1, 16:2 and 16:3.

RESULTS

Figure 2:
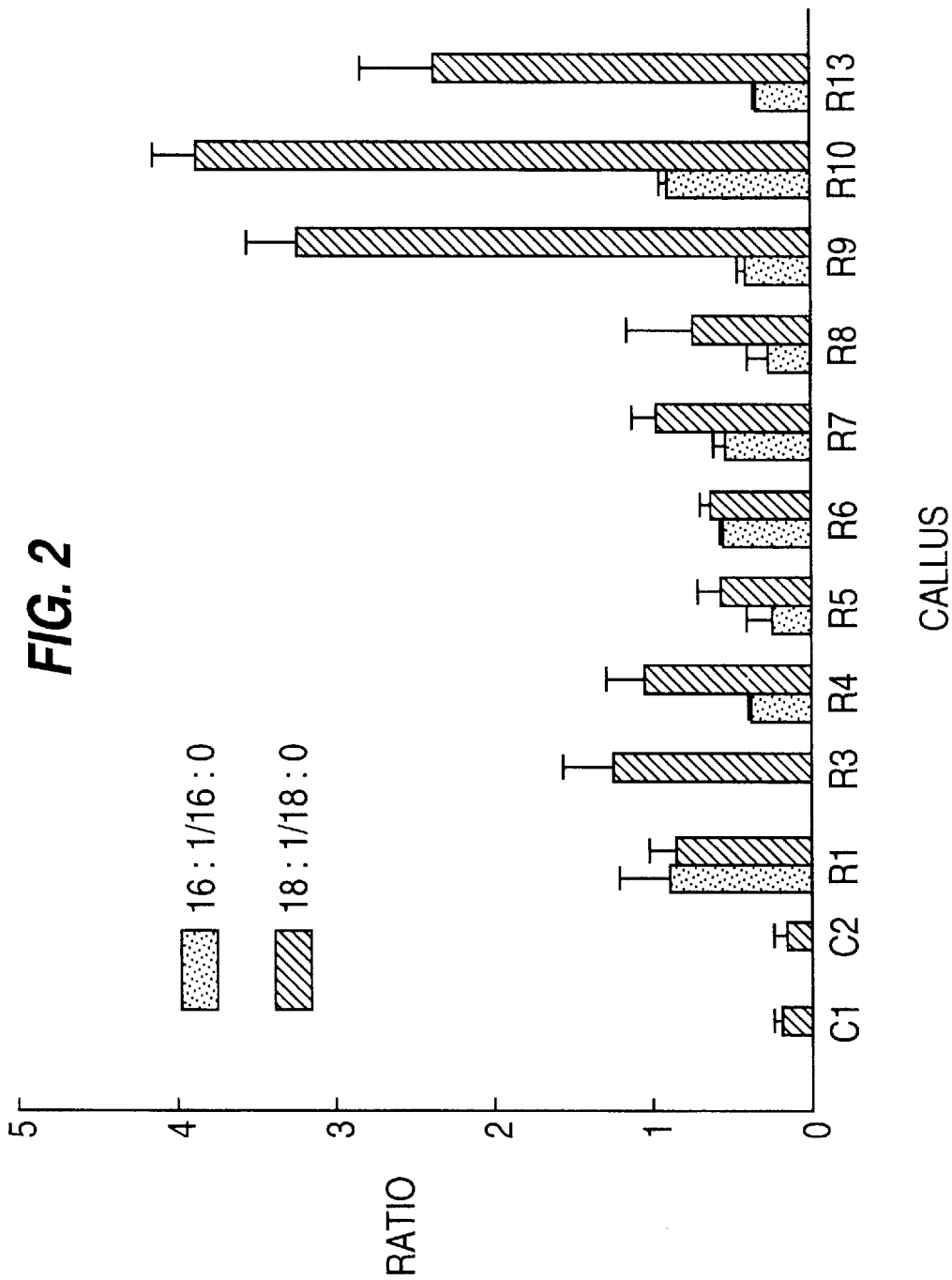
FIG. 2 is a bar graph depicting the results of the experiments of Examples 1–4, showing differences in 16:1/16:0 and 18:1/18:0 ratios in control and transformed callus tissue.

Following *Agrobacterium tumefaciens*-mediated transformation, kanamycin-resistant tobacco calli were screened for altered fatty acid composition. Several calli had higher ratios of 16:1/16:0 and/or 18:1/18:0 than controls (FIG. 2). The ratio of 18:1/18:0 could not be predicted from the 16:1/16:0 ratio. In nine of the ten desaturase transformants examined, the 18:1/18:0 ratio was higher than the 16:1/16:0 ratio, as was also seen in control calli. These data suggested that regenerated plants might also have altered fatty acid levels.

Figure 3:
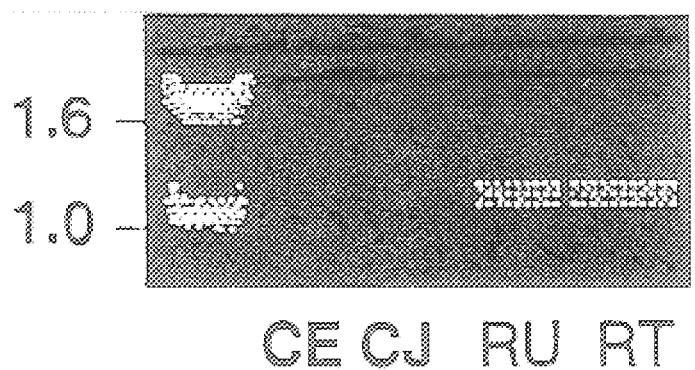
FIG. 3 depicts the results of the experiments of Examples 1–4, showing a computer-generated image from gels showing the presence of the gene of this invention as amplified by PCR.

Data indicating the presence of the introduced desaturase gene are presented in FIG. 3. PCR amplification of total plant DNA confirmed that the expected 1.1 kb product is not seen in 2 control plants transformed with a plasmid that lacks the rat desaturase gene. FIGS. 4 through 7 graphically depict data obtained from analysis of leaves from these same plants.

Figure 4:
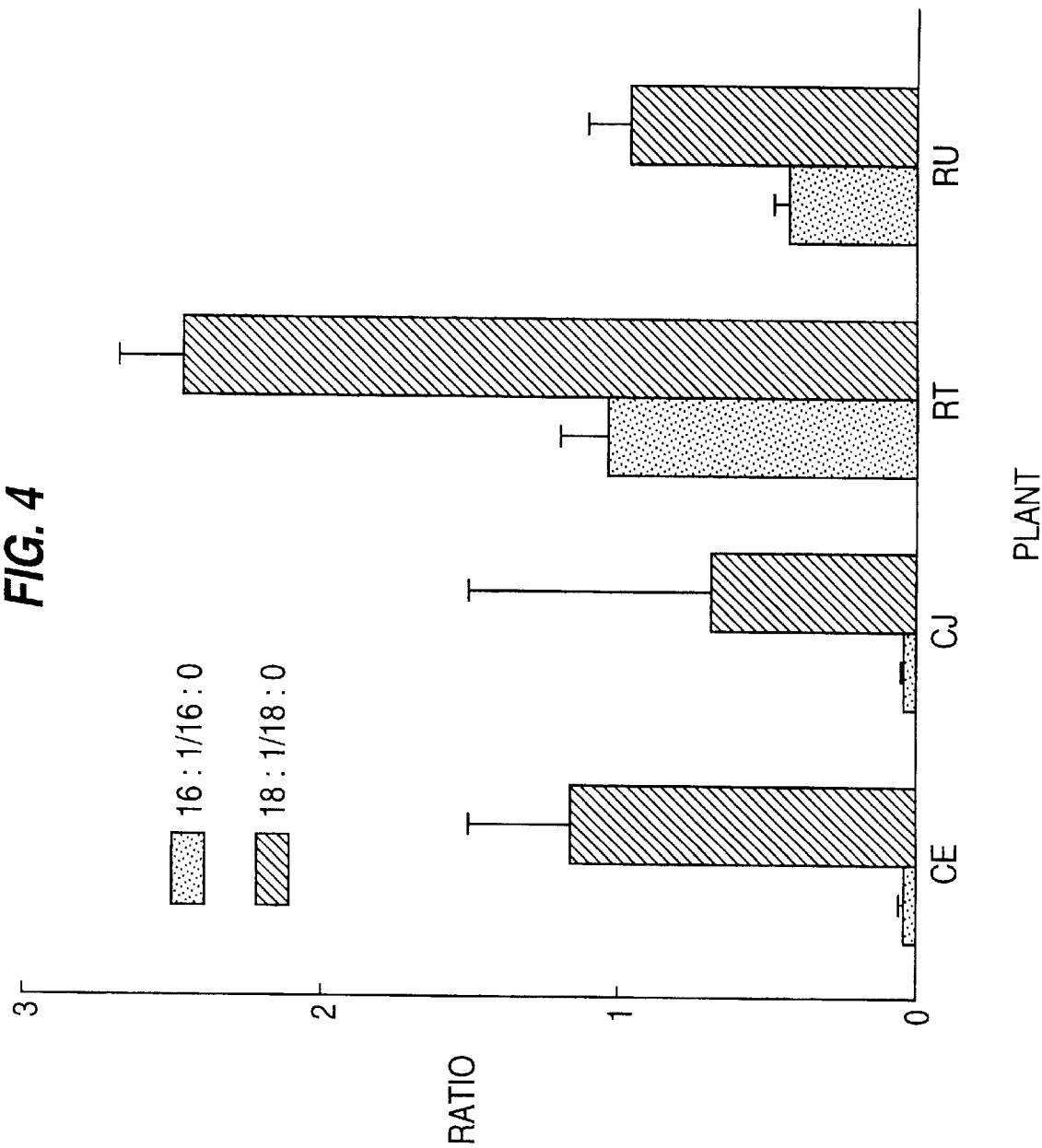
FIG. 4 is a bar graph depicting the results of the experiments of Examples 1–4, showing differences in 16:1/16:0 and 18:1/18:0 ratios in control and transformed plant tissue.

As with calli, leaves harboring the rat desaturase gene were hoped to have an increase in the 16:1/16:0 and/or the 18:1/18:0 ratios when compared to controls. FIG. 4 shows a clear increase in the 16:1/16:0 ratio for two plants (RT and RU) transformed with the rat desaturase gene. Plant RT has a higher 18:1/18:0 ratio than controls, while RU does not. This is in contrast to data from calli (FIG. 2), where 18:1/18:0 ratios were consistently higher in calli carrying the rat desaturase gene than in controls. However, the CaMV 35S promoter does not work as well in some differentiated tissues as it does in undifferentiated callus cells, and that may explain the difference.

Figure 5:
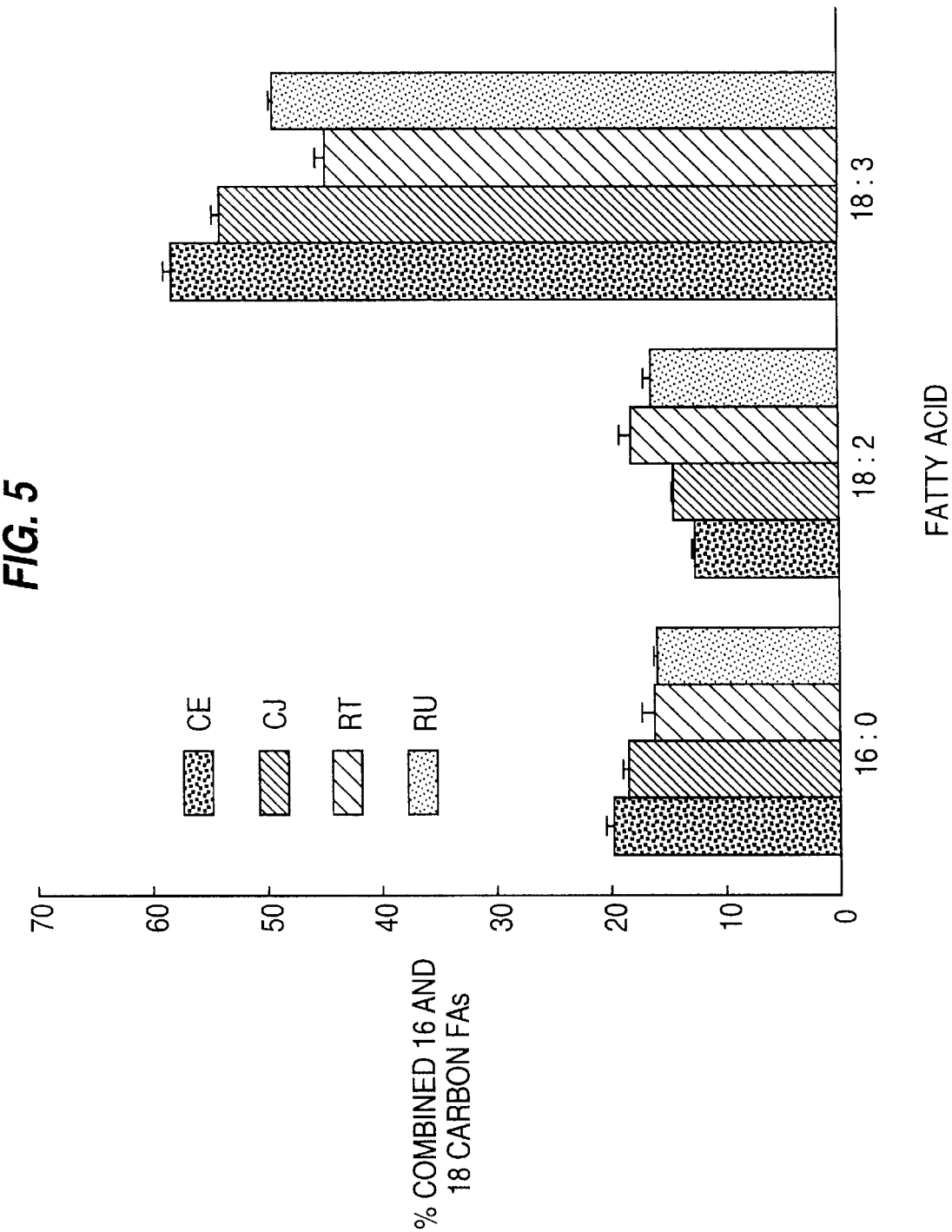
FIG. 5 is a bar graph depicting the results of the experiments of Examples 1–4, showing differences in 16:0, 18:2 and 18:3 fatty acid percentages in control and transformed plants.
Figure 6:
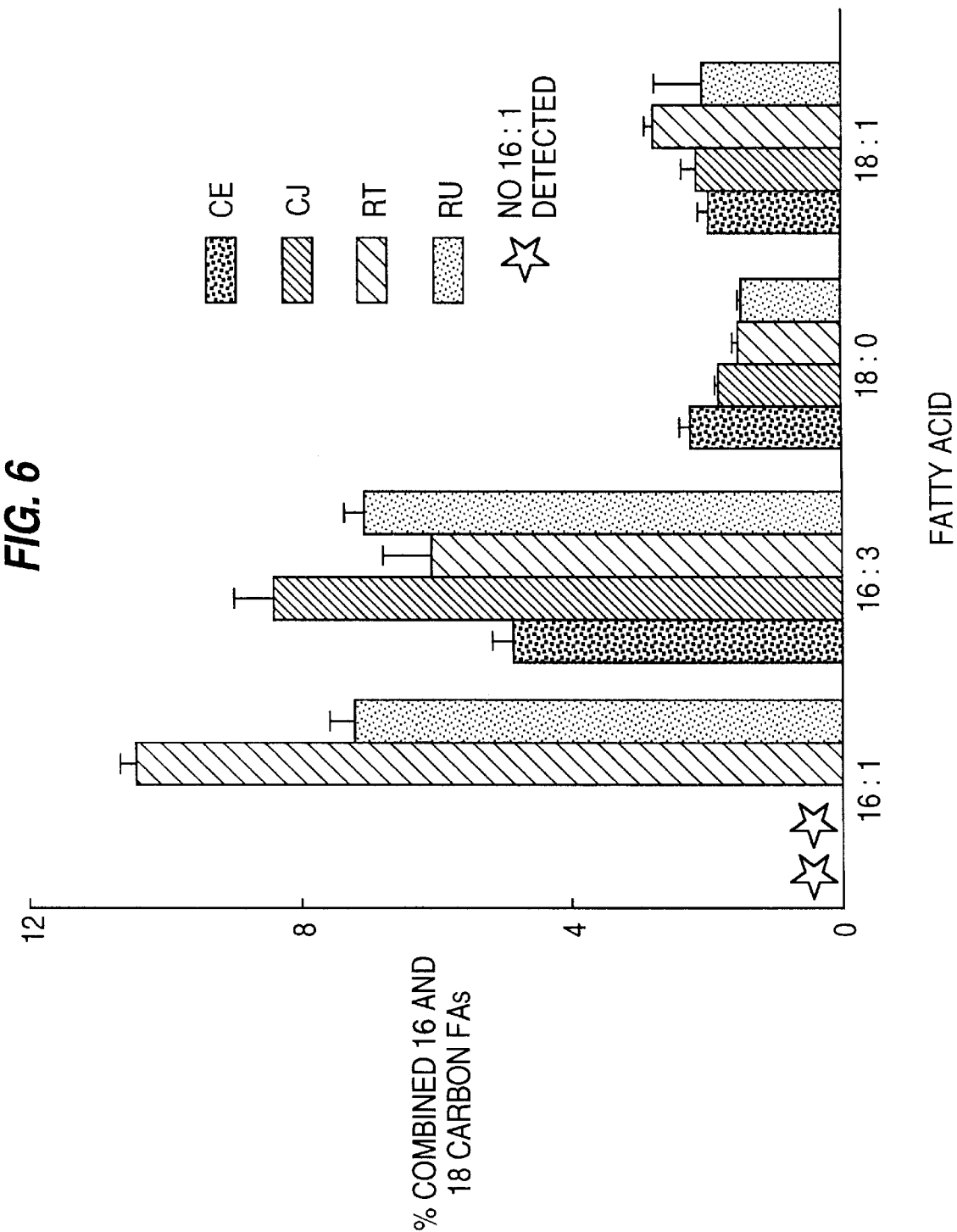
FIG. 6 is a bar graph depicting the results of the experiments of Examples 1–4, showing differences in 16:1, 16:3, 18:0 and 18:1 percentage levels between control and transformed plant tissue.

Since it was unknown what effect an introduced desaturase might have on fatty acid composition and levels, quantities of 16:0, 16:1, 16:2, 16:3, 18:0, 18:1, 18:2, and 18:3 were also determined. To visualize how these moieties changed, the amounts of 16:0, 16:1, 16:2, 16:3, 18:0, 18:1, 18:2, and 18:3 in tobacco leaves were combined and the amount of each fatty acid was expressed as a percentage of this total (FIG. 5 and 6). A large increase in 16:1 as well as a reduction in 16:0 and 18:0 can be seen in plants RT and RU. Levels of 18:2 also increased relative to controls. The desaturase transformants RT and RU also have a reduced percentage of 18:3 when compared to controls.

In order to obtain an overall view of lipid accumulation, 16 and 18 carbon fatty acids (16:0, 16:1, 16:2, 16:3, 18:0, 18:1, 18:2, and 18:3) were combined and expressed as mg FA per gram fresh weight or dry weight (data not shown). The similarity between total 16 and 18 carbon fatty acid levels in control and desaturase-transformed plants suggests a compensation between pathways involved in leaf lipid metabolism. Such a compensation has been implicated in various desaturase mutants of Arabidopsis [Science 252:80–87 (1991)].

To further indicate that elevated levels of 16:1 found in desaturase-transformed tobacco resulted from the product of the introduced gene, leaf lipids were fractionated into classes. Since 16:1 does not normally appear in plant phosphatidylcholine (PC), we examined this fraction in more detail, with results as illustrated in FIG. 6. It can be seen that 16:1 was only detected in PC from plants transformed with the rat desaturase gene. This qualitative difference between controls and desaturase transformants provides clear evidence that the introduced desaturase is functioning in leaf tissue. The presence of 16:1 in phosphatidylcholine from leaves transformed with the rat desaturase gene (FIG. 6) is a necessary requirement for changing seed lipid composition, which is primarily triglyceride. Phosphatidylcholine is the immediate precursor of triglyceride in developing seeds.

The ability to manipulate fatty acid composition in plants with a desaturase from rat demonstrates that an approach other than mutant selection can be used to alter plant lipid levels.

EXAMPLE 5

Figure 7:
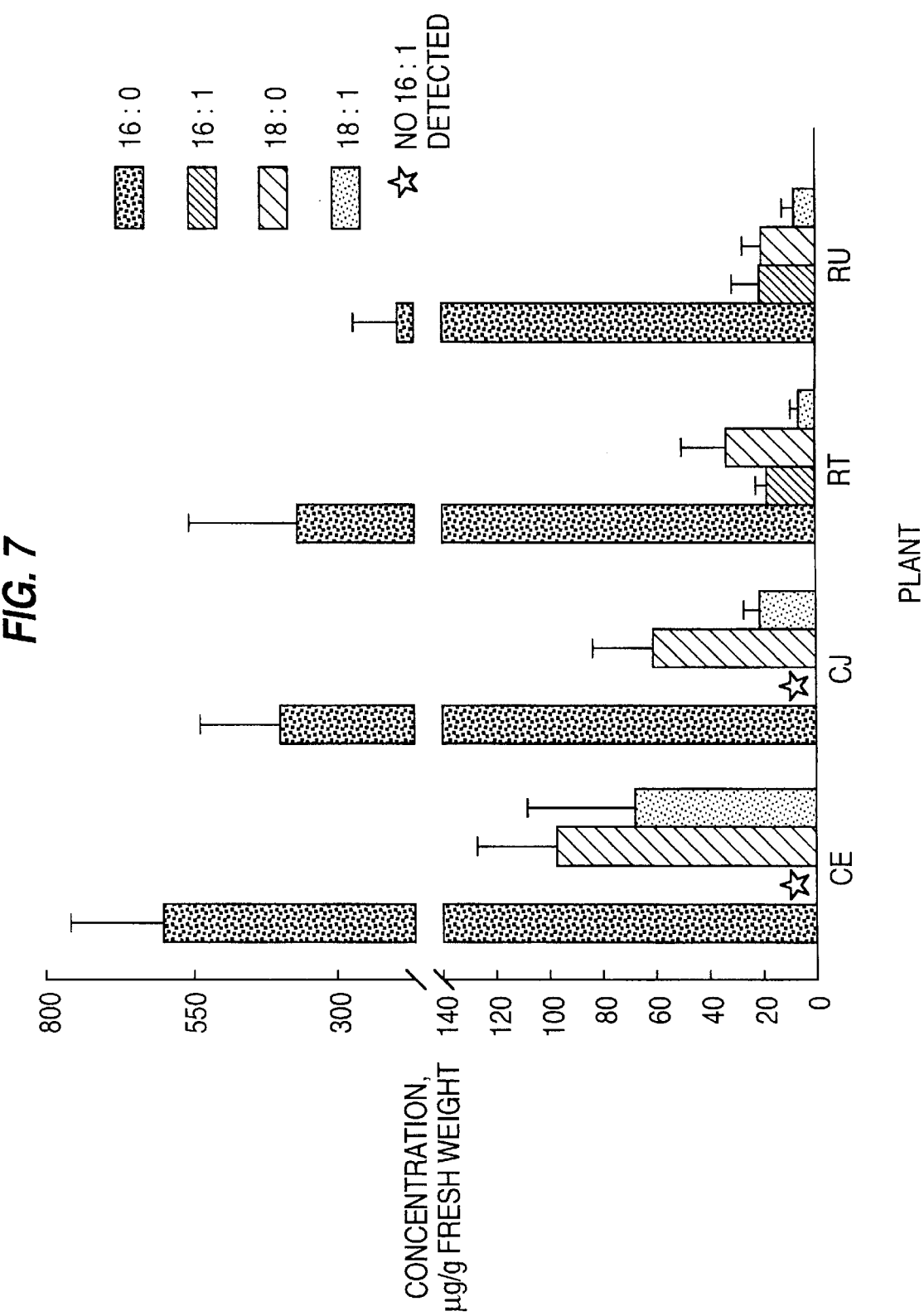
FIG. 7 is a bar graph depicting the results of the experiments of Examples 1–4, showing differences in 16:1/16:0 and 18:1/18:0 ratios in control and transformed plant tissue.
Figure 8:
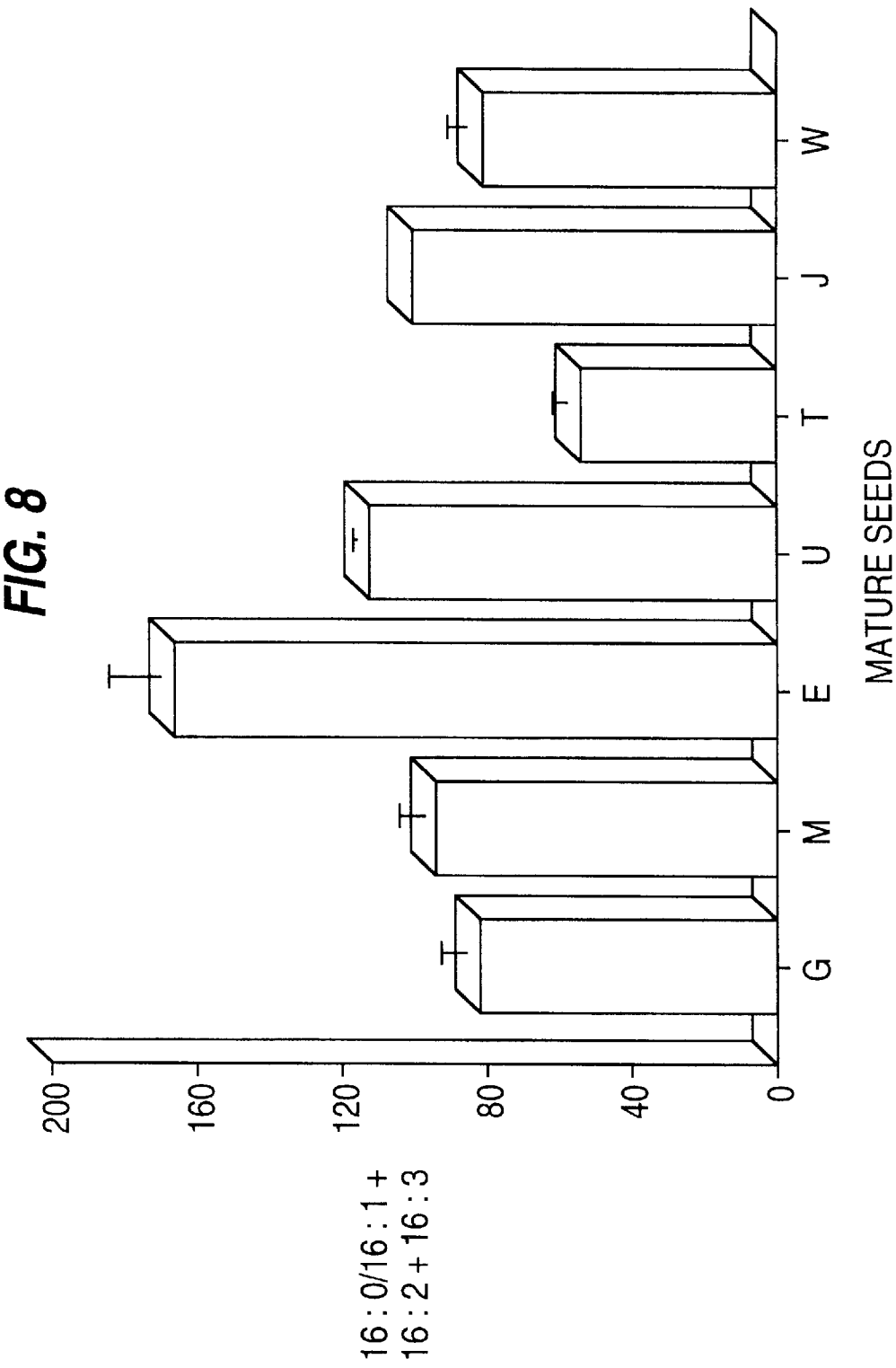
FIG. 8 is a bar graph depicting the results of the experiments of Examples 1–5, showing alterations of saturated to unsaturated fatty acid ratios in mature seed of the plants transformed according to this invention.

Seed from transgenic plants has also been examined and the dramatic increase in 16:1 fatty acid moieties in total leaf lipids is echoed in seed lipid, although at a lower level, as seen in FIG. 7. The desaturated/saturated fatty acid ratio has also been increased in representative desaturase transformants relative to control transgenic plant leaf and seed tissues (FIG. 7). This is further illustrated by observation of the saturated-to-unsaturated ratio of 16-carbon fatty acid moieties. As seen in FIG. 8, selected transgenic plants G, M, U, T, J, and W had large reductions in 16:0/(16:1 +16:2+ 16:3) compared to control plant E.

EXAMPLE 6

The plasmid pDs3–358, constructed as described in *J. Biol. Chem.*, 263:2532–2536, was provided by P. Strittmatter. This was digested with BamHI and SstI to release a 1.2 kb fragment that contained the rat desaturase gene. This was ligated to a previously made ACT vector, pALLNAPG1, to generate pALLNAPSCD; this process juxtaposed the stearyl COA desaturase coding portion directly behind the seed-specific promoter napin in a binary vector, ready for plant transformation.

A promoter-gene cassette carrying the napin promoter and stearyl CoA desaturase gene was excised as a HindIII-SstI fragment and used to replace the HindIII-SstI fragment of a binary vector, pALLTKrep, to generate pALLTKNAPSCD, which was structurally and functionally equivalent to pALLNAPSCD except it provided cleaner selection for transgenic plants on kanamycin antibiotic. Transfer of the DNA into Agrobacterium was accomplished by transformation directly into the organism, as opposed to triparental mating as described above. The gene was inserted into canola cells by cell wounding and cocultivation, and whole canola transformants were regenerated from the transformed callus cultures. Seeds were obtained from the resulting regenerated transformed plants.

What is claimed is:

1. A chimeric expression cassette comprising (1) a DNA molecule encoding Δ-9 fatty acid desaturase, wherein said Δ-9 fatty acid desaturase is a rat or yeast Δ-9 fatty acid desaturase and (2) regulatory nucleotide sequences, wherein said DNA molecule is operably linked to said regulatory sequences, and wherein said regulatory sequences are capable of stimulating the expression of said Δ-9 fatty acid desaturase in plant cells.

2. An expression vector, comprising the expression cassette of claim 1.

3. Transformed plant cells comprising the expression vector of claim 1, wherein said Plant cells express said Δ-9 fatty acid desaturase.

4. The transformed plant cells of claim 3, wherein said cells are the cells of a monocotyledonous species.

5. The transformed plant cells of claim 4, wherein said monocotyledonous species is selected from the group consisting of maize, sorghum, wheat, palm and rice.

6. The transformed plant cells of claim 3, wherein said cells are the cells of a dicotyledonous species.

7. The transformed plant cells of claim 6, wherein said dicotyledonous species is selected from the group consisting of soybean, rapeseed, jojoba, Chinese tallow tree, tobacco, safflower, peanut and sunflower.

8. An in vitro culture comprising the transformed plant cells of claim 7.

9. A transformed soybean plant, wherein time cells of said plant comprise the expression cassette of claim 1, and wherein said plant cells express said Δ-9 fatty acid desaturase.

10. A transformed rapeseed plant, wherein the cells of said plant comprise the expression cassette of claim and wherein said plant cells express said Δ-9 fatty acid desaturase.

11. A transformed sunflower plant, wherein the cells of said plant comprise the expression cassette of claim 1, and wherein said plant cells express said Δ-9 fatty acid desaturase.

12. A transformed safflower plant, wherein the cells of said plant comprise the expression cassette of claim 1, and wherein said plant cells egress said Δ-9 fatty acid desaturase.

13. A transformed peanut plant, wherein the cells of said plant comprise the expression cassette of claim 1, and wherein said plant cells egress said Δ-9 fatty acid desaturase.

14. A method of increasing the percentage compositions of unsaturated fatty acid moieties and corresponding fatty acid-derived lipids in plant cells, comprising the step of introducing a DNA molecule comprising the chimeric expression cassette of claim into said plant cells to produce transformed cells.

15. The method of claim 14, further comprising the step of producing whole plants from transformed plant cells, wherein said plants comprise cells that express said Δ-9 fatty acid desaturase.

16. The method of claim 15, further comprising the step of sexually or clonally reproducing said whole plants, wherein the progeny of said whole plants comprise cells that express said Δ-9 fatty acid desaturase.

17. The method of claim 14, wherein said expression cassette is introduced into said cells by electroporation.

18. The method of claim 14, wherein said expression cassette is introduced into said cells by microparticle bombardment.

19. The method of claim 14, wherein said expression cassette is introduced into said cells by microinjection.

20. A method for increasing the percentage compositions of unsaturated fatty acid moieties and corresponding fatty acid-derived lipids in Agrobacterium-susceptible dicotyledonous plants, comprising the step of infecting cells of said plants with Agrobacteria that comprise the expression cassette of claim 1.

* * * * *

UNITED STATES PATENT AND TRADEMARK OFFICE
CERTIFICATE OF CORRECTION

PATENT NO. : 5,866,789
DATED : February 9, 1999
INVENTOR(S) : David F. Hildebrand, et. al.

It is certified that error appears in the above-indentified patent and that said Letters Patent is hereby corrected as shown below:

Title page, item [54] and col. 1, line 1, "9" should read --Δ9--.
Column 9, Claim 3, line 2, "Plant" should read --plant--;
Column 10, Claim 9, line 1, the word "time" should be changed to --the--;
Column 10, Claim 10, line 2, insert --1-- after the word claim;
Column 10-11, Claim 14, line 5, insert --1-- after the word claim; and
Column 11, Claim 15, line 2, insert the word "said" after the word from.

Signed and Sealed this

Nineteenth Day of October, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 31 bases
        ( B ) TYPE: nucelotide
        ( C ) STRANDEDNESS: single
        ( D ) TOPOLOGY: linear ( i i ) MOLECULE TYPE: synthetic DNA ( i i i ) HYPOTHETICAL: No ( i v ) ANTI-SENSE: No ( x ) PUBLICATION INFORMATION:
        ( A ) AUTHORS: Stritmatter et al.
        ( C ) JOURNAL: J. Biol. Chem.
        ( D ) VOLUME: 263
        ( F ) PAGES: 2532-2536
        ( G ) DATE: 1988

( x i ) SEQUENCE DESCRIPTION: SEQ ID. NO: 1:

ACGTGGATCC ACCATGCCGG CCCACATGCT C         31

( 2 ) INFORMATION FOR SEQ ID NO: 2:

( i ) SEQUENCE CHARACTERISTICS:
        ( A ) LENGTH: 18 bases
        ( B ) TYPE: nucelotide
        ( C ) STRANDEDNESS: single
        ( D ) TOPOLOGY: linear ( i i ) MOLECULE TYPE: synthetic DNA ( i i i ) HYPOTHETICAL: No ( i v ) ANTI-SENSE: Yes ( x ) PUBLICATION INFORMATION:
        ( A ) AUTHORS: Stritmatter et al.
        ( C ) JOURNAL: J. Biol. Chem.
        ( D ) VOLUME: 263
        ( F ) PAGES: 2532-2536
        ( G ) DATE: 1988

( x i ) SEQUENCE DESCRIPTION: SEQ ID. NO: 2:

GCTACTCTTG TGGCTCCC         18